(12) United States Patent
Weersink et al.

(10) Patent No.: US 6,219,566 B1
(45) Date of Patent: Apr. 17, 2001

(54) METHOD OF MEASURING CONCENTRATION OF LUMINESCENT MATERIALS IN TURBID MEDIA

(75) Inventors: Robert A. Weersink, Toronto; Michael S. Patterson, Ancaster, both of (CA)

(73) Assignee: Photonics Research Ontario, Toronto (CA)

( * ) Notice: Subject to any disclaimer, the term of this patent is extended or adjusted under 35 U.S.C. 154(b) by 0 days.

(21) Appl. No.: 09/352,606

(22) Filed: Jul. 13, 1999

(51) Int. Cl.[7] .................................................. A61B 5/00
(52) U.S. Cl. .................. 600/317; 600/322; 600/310; 356/317
(58) Field of Search .................................. 600/310, 317, 600/322, 323, 344, 476; 356/311, 317, 318; 250/252.1

(56) References Cited

U.S. PATENT DOCUMENTS

| | | |
|---|---|---|
| 4,476,870 | 10/1984 | Peterson et al. . |
| 4,768,513 | 9/1988 | Suzuki . |
| 5,203,328 | 4/1993 | Samuels et al. . |
| 5,280,788 | 1/1994 | Janes et al. . |
| 5,290,275 | 3/1994 | Kittrell et al. . |
| 5,419,323 | 5/1995 | Kittrell et al. . |
| 5,582,168 | 12/1996 | Samuels et al. . |
| 5,894,340 | 4/1999 | Loree et al. . |
| 6,070,093 * | 5/2000 | Oosta et al. .......................... 600/310 |

* cited by examiner

Primary Examiner—Eric F. Winakur
(74) Attorney, Agent, or Firm—Lynn C. Schumacher; Hill & Schumacher

(57) ABSTRACT

The present invention provides a method for measurement of concentration of fluorophores in turbid media. The method uses a fluorescence plus reflectance technique to measure quantitatively the in vivo concentration of a fluorescent drug independent of the tissue optical properties. The method involves using the reflectance measurement as a means of correcting for tissue scattering and absorption in the fluorescence measurement. Light directed to the tissue by means of an optical fiber to excite the fluorophores. Fluorescence from the fluorophores is measured by another fiber at a distance (D1) from the source in the turbid medium, while the excitation light is simultaneously collected at a distance (D2) from the source. The ratio fluorescence/reflectance will be approximately constant for a fixed concentration of the fluorophore and a judicious choice of D1 and D2, regardless of the optical properties of the tissue. The ratio of fluorescence to reflectance on a tissue sample is compared to a calibration curve for a range of fluorophore concentrations, in order to estimate the in vivo concentration in the turbid medium. The optimum distances D1 and D2 are obtained by constructing several sample turbid mediums with known optical properties mimicking the optical properties of the samples on which the measurements are to be made. Fluorescence and reflectance measurements are performed at several distances from the excitation point for all turbid samples and a best fit obtained for each pair of distances with pairs exhibiting the lowest values of sum of squares of residuals lower than a threshold being used.

35 Claims, 12 Drawing Sheets

| DISTANCE PAIRS | |
|---|---|
| FLUORESCENCE / REFLECTANCE | STANDARD DEVIATION |
| ● 0.86 mm / 1.42 mm | 0.044 |
| ▲ 0.86 mm / 0.86 mm | 0.118 |
| ○ 1.42 mm / 0.86 mm | 0.131 |
| □ 1.42 mm / 1.42 mm | 0.050 |

METHOD OF MEASURING CONCENTRATION OF LUMINESCENT MATERIALS IN TURBID MEDIA

FIELD OF THE INVENTION

The present invention relates to a method and device for measuring concentrations of luminescent materials in turbid media, and more particularly the invention relates to measurement of fluorophore concentrations in turbid media such as tissue in vivo using a combined fluorescence/reflectance measurement technique.

BACKGROUND OF THE INVENTION

Light directed into a turbid medium undergoes two phenomena; scattering and absorption. In tissue, for example, the amount of scattering is determined by the tissue structure such as cell and mitochondria size, while the absorption is determined by the quantity of endogenous absorbers such as melanin and porphyrins (e.g. hemoglobin in blood). Different tissue types scatter and absorb light in different amounts, i.e. liver versus muscle. Many recent pharmacokinetic studies are using fluorescent drugs to monitor body processes. Also, new forms of cancer treatments use fluorescent drugs. These treatment methods require accurate knowledge of the drug concentration for proper treatment.

A possible method of determining the concentration of the fluorescent drug is to measure its fluorescence. The strength of the fluorescence signal however, will depend on the intensity of excitation light, and the scattering and absorption properties of the turbid medium.

U.S. Pat. No. 4,178,917 to Shapiro discloses a method and system for non-invasive detection of zinc protoporphyrins using an excitation beam and two detectors, one being termed the reference detector for measuring scattered or reflected light $S_2$ at the excitation wavelength. The fluorescence detector measures the fluorescence $S_1$ from the red blood cells flowing through the measurement volume. The intent of this device, therefore, is to measure only the concentration of fluorophores within the blood stream and not in the surrounding tissue. As a result, the signal is influenced by the intervening tissues and the method described does not correct for differences in these tissues. A further drawback to this method is that it is not readily adaptable for measuring fluorophore concentrations in a wide range of turbid media.

It would therefore be very advantageous to provide a method for measuring in vivo concentration of a luminescent material in a turbid medium substantially independent of the scattering and absorption properties of the medium.

SUMMARY OF THE INVENTION

It is an object of the present invention to provide a non-invasive measurement of the concentration of a luminescent compound in a turbid medium regardless of the scattering and absorption properties of the medium.

In one aspect of the invention there is provided a method of measuring concentration of a luminescent compound in a turbid medium, comprising:

illuminating a turbid medium with a beam of light having an effective wavelength $\lambda_1$ to excite luminescence in a luminescent compound being detected in the turbid medium;

measuring a luminescence signal F an effective distance of about D1 from the beam of light;

measuring a reflectance signal R at wavelength $\lambda_1$ an effective distance of about D2 from the beam of light wherein the distances D1 and D2 are selected to reduce effects of scattering and absorption variations between turbid samples; and processing the measured R and F signals to produce an effective function f(F, R) and comparing f(F, R) to a calibration curve of $f_c(F_c, R_c)$ versus concentration of the luminescent compound in a turbid medium to determine a concentration of the luminescent compound.

In another aspect of the present invention there is provided a method of determining pairs of distances D1 and D2 for measuring luminescence and reflectance respectively in order to reduce effects of scattering and absorption variations between turbid samples, the distances D1 and D2 being measured from a beam of light used to induce luminescence in one or more luminescent compounds in the turbid medium, the method comprising the steps of;

a) providing an effective reference turbid media having optical properties mimicking the turbid media and adding known amounts of a luminescent compound so as to increase the concentration of the luminescent compound and after addition of each known amount exciting the reference turbid medium with a beam of light at an effective wavelength and measuring a luminescence signal at a plurality of distances D1 from the beam of light and measuring a reflectance signal at a plurality of distances D2 from the beam of light;

b) repeat step a) for an effective number of reference turbid media possessing a range of optical properties;

c) for each pair of distances,
plot an effective function of both luminescence and reflectance (f(F, R)) versus concentration of the luminescent compound for all the reference turbid media and perform a regression analysis to calculate a best fit function and calculate a sum of squares of residuals; and d) identify pairs of distances D1 and D2 corresponding to values of sum of squares of residuals lower than a threshold value for use in measuring luminescence and reflectance in the turbid medium in which concentration of the luminescent compound is to be determined.

The present invention also provides a device for measuring concentration a light source for producing a beam of light of wavelength $\lambda_1$;

first detector means for measuring fluorescence;

second detector means for measuring light of wavelength $\lambda_1$; and a holder for holding the light source, first and second detector means, the holder including a planar portion adapted to be placed on a surface of a tissue and an adjustment mechanism for adjusting a distance between the light source and the first detector and a distance between the light source and the second detector; and processing means connected to said first and second detector means for processing measured fluorescence signals from said first and second detector means and calculating therefrom a concentration of a fluorescent compound in a tissue.

BRIEF DESCRIPTION OF THE DRAWINGS

The invention will now be described, by way of non-limiting examples only, reference being had to the accompanying drawings, in which.

DETAILED DESCRIPTION OF THE INVENTION

Referring first to FIG. 1, the preferred embodiment of the method of the present invention uses a fluorescence plus reflectance technique to measure quantitatively the in vivo concentration of a fluorescent drug or photosensitizer (ps), (both referred to hereinafter as fluorophores) independent of the tissue optical properties. The basic principle involves using the reflectance measurement as a means of correcting for tissue scattering and absorption in the fluorescence measurement. In practice, a non-invasive probe is placed on the tissue surface, and light directed to the tissue by means of an optical fiber. This light is used to excite the fluorophores. Fluorescence from the fluorophores is measured via another fiber at a known distance (D1) from the excitation fiber, while the excitation light is simultaneously collected at a larger distance (D2). The excitation light measured at D2 is referred to as the reflectance R since it is due to light at the excitation wavelength undergoing scattering/reflection within the body of the tissue and is not referring to specular reflectance from the surface of the tissue. Therefore, as defined herein the term "reflectance" is being used even though the quantity may be measured in the interior of the turbid medium rather than at its surface.

The inventors have made the unexpected finding that, to a first approximation, the correct choice of D1 reduces the effect of scattering and the correct choice of D2 corrects for the reduction in fluorescent intensity that would accompany an increase in tissue absorption. The distances D1 and D2 are relative to the excitation position on the surface of the turbid medium and are independent of each other. Therefore, D1 and D2 define the radii of two circles about the excitation or source position upon which the collection fibers may be positioned.

Figure 1A:
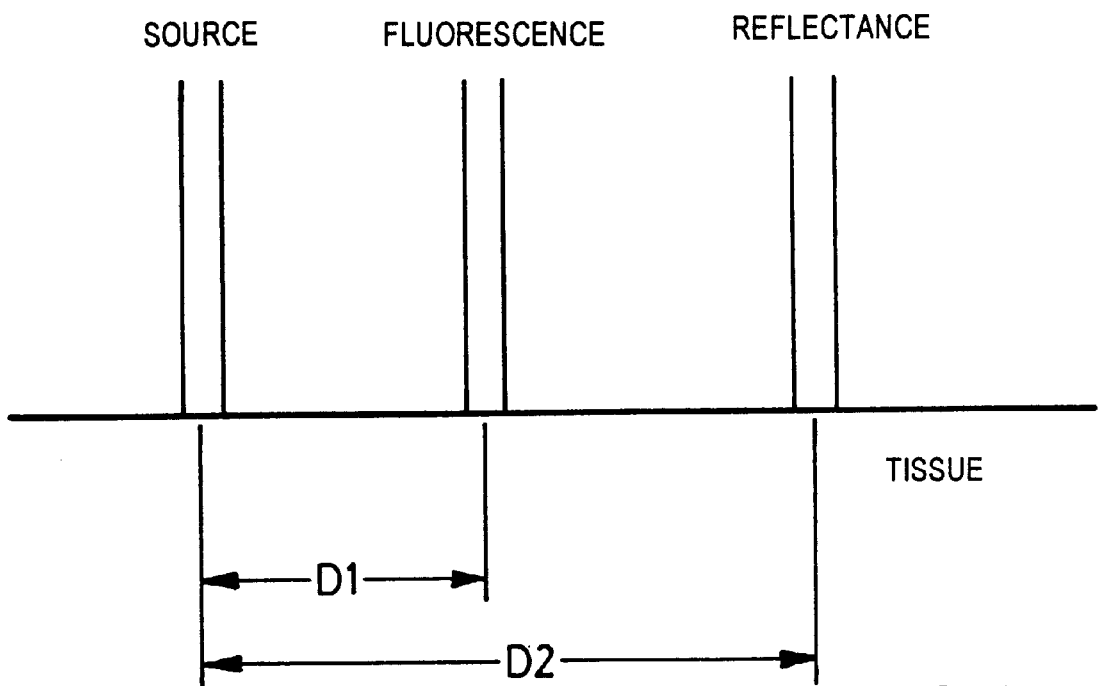
FIG. 1a is a diagrammatic representation showing the relative relationship between excitation source and detectors for measuring reflectance and fluorescence according to the method of the present invention.

In the method embodied in the diagrammatic representation in FIG. 1a, the excitation light is directed into the tissue at an angle substantially perpendicular to the surface of the tissue, while the fluorescence and reflectance light are collected perpendicular to the surface. The light may also be directed into the tissue at an angle other than normal incidence and collected at angles other than those normal to the surface. In such a case, the distances D1 and D2 may be different than those for the case where the illumination and collection light is normal to the surface.

Figure 1B:
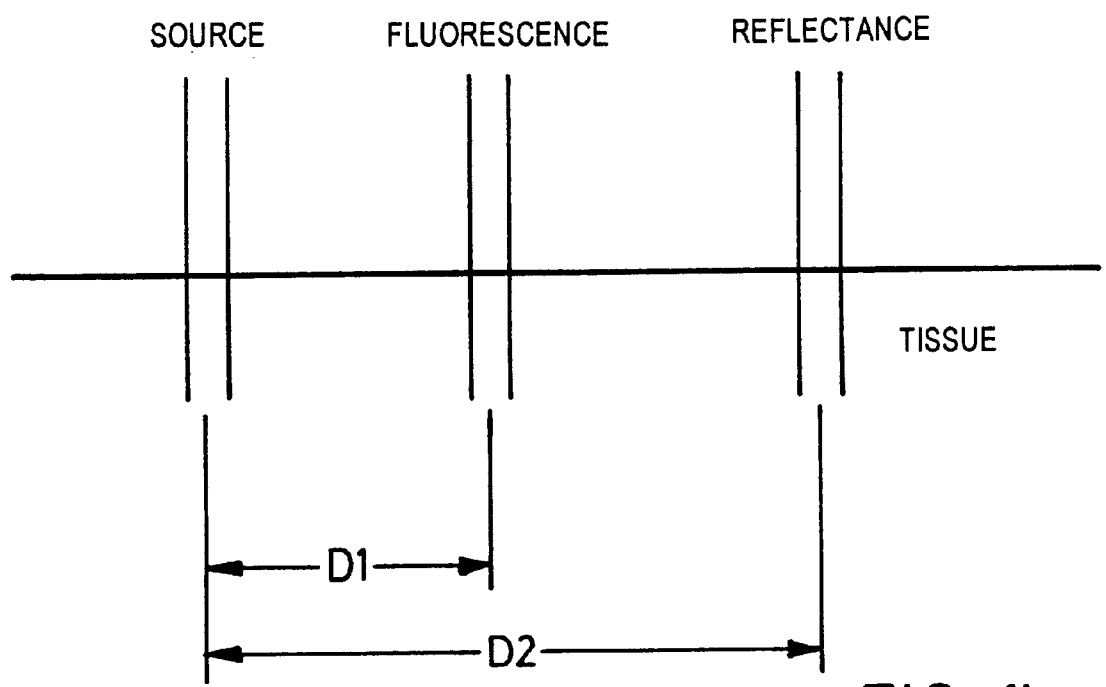
FIG. 1b shows an interstitial embodiment in which the fibers are located in the turbid medium

FIG. 1b shows another embodiment of the invention. As in the above embodiment, three fibers are used; one to deliver excitation light to the medium, one to collect the fluorophore fluorescence at a distance D1 and one to collect the excitation light at a distance D2. This embodiment differs from the one described above in that now the three fibers are placed in the tissue so that while the device used in FIG. 1a may be considered non-invasive, the device in FIG. 1b may be invasive. The distances D1 and D2 are likely to be different from that used in the non-invasive embodiment described above, but there will be a choice of D1 and D2 such that the ratio of fluorescence/reflectance is a constant for fixed concentration of fluorophore. FIG. 1b shows the ends of the three fibers placed at the same depth in the turbid medium. In practice, there would be no restriction on the relative vertical placement of the three fibers.

For a fixed concentration of the fluorophore, and a judicious choice of D1 and D2, the ratio of fluorescence/reflectance will be approximately constant, regardless of the optical properties of the tissue. A calibration curve is made by measuring fluorescence and reflectance for a range of fluorophore concentrations in a variety of turbid liquid samples and plotting the ratio F/R as a function of concentration of the fluorophore (luminescent material). A user can then make a measurement of a tissue sample, compare the ratio to that of the calibration curve, and estimate the in vivo concentration.

Figure 2:
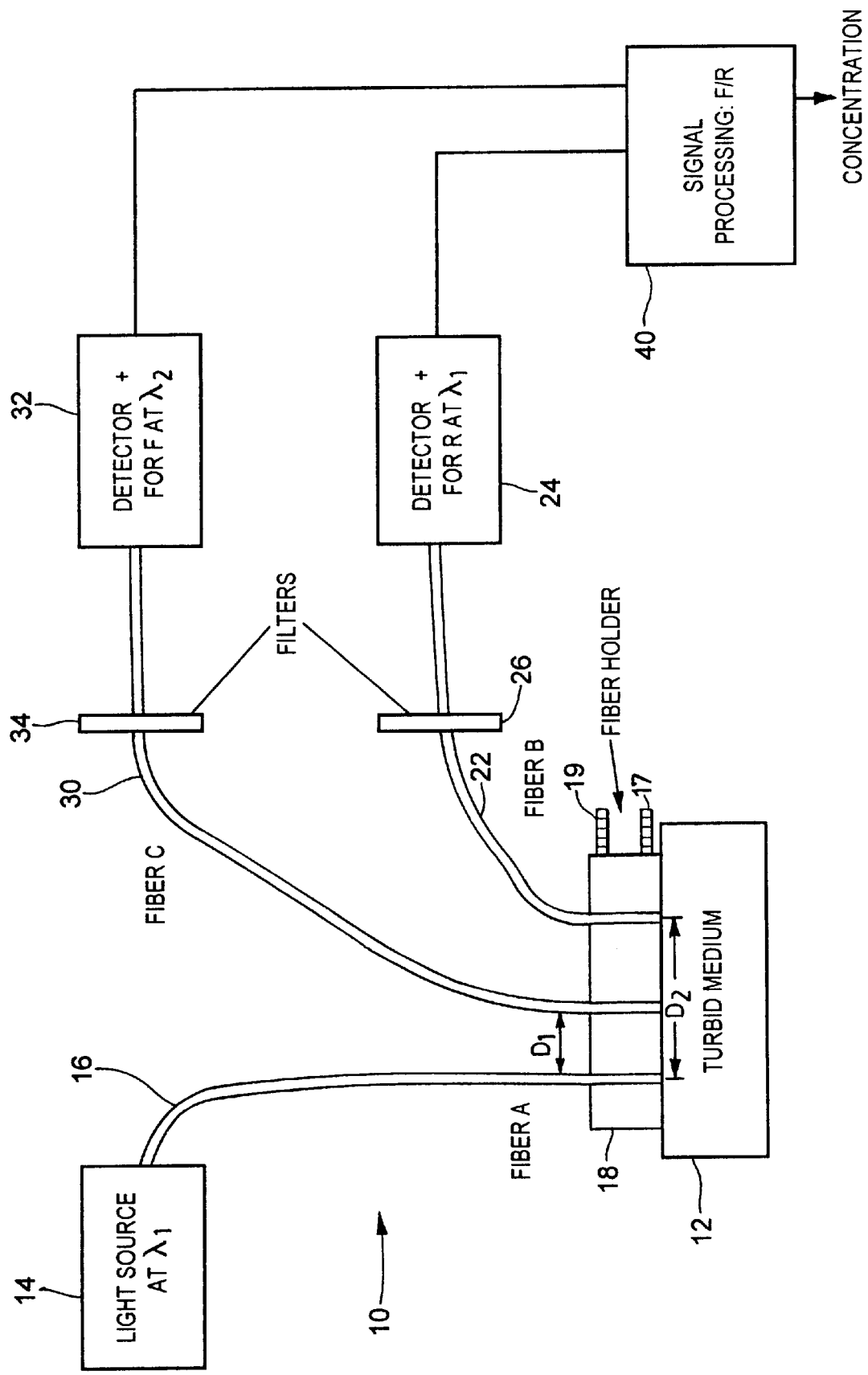
FIG. 2 is a block diagram showing an apparatus for measuring fluorophore concentrations in turbid media constructed in accordance with the present invention.

Referring to FIG. 2, a device 10 is shown for measuring concentration of fluorophores in a turbid medium 12. Device 10 includes a light source 14 for delivering excitation light at wavelength $\lambda_1$ to the surface of the turbid medium 12 (i.e. tissue). The excitation light at wavelength $\lambda_1$ is delivered from source 14 to turbid medium 12 by an optical fiber 16 which is coupled to source 14 at one end and at the other end is held in probe 18 at an angle perpendicular to the face of the probe. The probe is positioned in contact with the surface of a patient's skin.

Another optical fiber 22 is placed a distance of 1.4 to 1.45 mm away from fiber 16 and is held in the probe at angle perpendicular to the face of the probe. Fiber 22 is connected to a detector 24. An adjustment mechanism 17 provides for adjustment of the distance D1 between the distal end portion of fiber 22 located adjacent to the tissue surface with respect to the distal end portion of source fiber 16 located adjacent to the tissue surface. The purpose of fiber 22 is to collect the excitation light at $\lambda_1$ that has traveled through the turbid medium 12 and back to the surface of the medium. This signal is called the reflectance, R. Since both reflectance and fluorescence signals will be collected or by fiber 22, separation of the reflectance signal at $\lambda_1$ from the fluorescence signals is necessary and may be achieved in any one of several ways. These include a band pass filter 26 that allows only light at $\lambda_1$ to pass through to the detector 24; a monochromator (not shown) set to allow only light at $\lambda_1$ to pass through to the detector; a combination of band pass filter and monochromator (not shown); a combination of spectrometer and detector array, such as a photodiode array or charge-coupled device array; and a combination of band pass filter, spectrometer and detector array.

Another optical fiber 30 is placed a distance of 0.84 to 0.88 mm away from fiber 16 and is held in the probe at an angle perpendicular to the face of the probe. The end face of fiber 30 is non-reflecting. An adjustment mechanism 19 provides for adjustment of the distance D2 between the distal end portion of fiber 30 located adjacent to the tissue surface with respect to the distal end portion of source fiber 16. Fiber 30 is connected to a detector 32 and the purpose of fiber 30 is to collect the fluorescence at $\lambda_2$ that has traveled through the turbid medium and back to the surface of the medium. This signal is called the fluorescence, F, since typically this light is due to fluorescence of the fluorophores excited at $\lambda_1$. Since both reflectance and fluorescence will be collected by fiber 30, separation of the fluorescence from the reflectance may be achieved in one of several ways. These include a band pass filter 34 that allows only light at $\lambda_2$ to pass through to the detector 32; a monochromator (not shown) set to allow only light at $\lambda_2$ to pass through to the detector; a combination of band pass filter and monochromator (not shown); a combination of spectrometer and detector array (not shown), such as a photodiode array or charge-coupled device array; and a combination of band pass filter, spectrometer and detector array.

In apparatus 10, the ends of the excitation fiber 16 and collection fibers 22 and 30 are positioned in the probe so that they are perpendicular to the fiber holder 18 and hence perpendicular to the tissue surface. If the fibers are positioned at different angles, then the distances noted in the description above for D1 and D2 will be different. These distances can be determined by following the procedure described hereinafter.

The signal output from detector 24 and the signal output from detector 32 are connected to a signal processor 40 for calculating the ratio F/R. The optical fibers 16, 22 and 30 used are typically 100 to 400 $\mu$m in diameter. The excitation light at $\lambda_1$ is preferably selected to match the electronic absorption band of the fluorophore. The light source 14 may be a low intensity laser at $\lambda_1$, a light emitting diode at $\lambda_1$, or a white light lamp source, with a band pass filter (not shown) placed along the delivery path such that only light at $\lambda_1$ is delivered to the surface of turbid medium 12. The detectors 24 and 32 may include but are not restricted to be a photodiode detector, a charge coupled device (CCD) detector or a photomultiplier tube (PMT).

In operation, the excitation light at $\lambda_1$ excites a fluorophore in the turbid medium such that it produces fluorescence at a second wavelength, $\lambda_2$. The fluorophores are typically exogenous to the turbid medium. For example, the fluorophore may be a fluorescent drug in tissue. The ratio of the collected signals, F/R, is then used to determine the concentration of the exogenous fluorophore in the turbid medium by comparing the measured ratio to that of a calibration curve of concentration versus F/R. The calibration curve of $f_c(F_c, R_c)$ versus concentration of the fluorophore is determined by measuring the fluorophore fluorescence in a turbid liquid sample, in which the concentration of the fluorophore can be controlled and varied by the addition of small aliquots of the fluorophore to the turbid sample. Measurements of the ratio F/R on the sample at different fluorophore concentrations then gives a simple plot of F/R versus concentration. In principle, calibration measurements only need to be made on one turbid sample. In practice, they may be made on a series of turbid liquid samples that have a variety of scattering and absorption properties. Doing so increases the certainty that the correct calibration curve has been generated.

While the preferred embodiment of the invention disclosed herein is a combined fluorescence/reflectance measurement, it will be understood that the method described can be more generally applied to the measurement of the concentration of compounds that emit light through phosphorescence. Therefore, this method can be used generally for quantification of luminescent compounds in turbid media that emit light either by fluorescence or phosphorescence.

A significant advantage of the present method and device over the prior art is achieved by the presence of fiber 22 and measuring the ratio F/R which minimizes the changes in fluorescence signal due to differences in scattering and absorption properties between different samples. The distances noted above have been found to be the best match for removing the scattering and absorption variations. Other distances have been tried but have not been found to be as effective.

Consider a device with only fibers 16 and 30 absent fiber 22. If the intensity of the light delivered down fiber 16 were to vary, the strength of the fluorescence signal F would also vary, even if the concentration of the fluorophore was a constant. If signal F were measured on liver tissue and on muscle tissue, and if both tissue samples had the same concentration of the fluorophore, signal F would be smaller with the liver measurement than with the muscle measurement because liver tissue absorbs light more strongly than muscle. The presence of fiber 22 to measure reflectance R and using the ratio F/R eliminates both of these problems. Even if the intensity of the excitation light varies, the strength of signals R and F will vary linearly with this change. Hence, taking the ratio of these two signals removes any variations or instabilities in the excitation light intensity. Therefore the method of the present invention advantageously reduces the effect of signal variations due to variations in excitation light source intensity without elaborate signal processing or excitation light monitoring techniques and it reduces the effect of variations in the fluorescence signal due to measuring on different tissue types.

The present invention provides a measurement of the in vivo concentration of a fluorophore in a turbid medium regardless of the scattering and absorption properties of the medium. An advantage of the method is that the measurement can be made non-invasively from the surface of the turbid medium so that in for example medical applications, this method can be used for non-invasively measuring in vivo drug concentrations without the use of biopsies.

The present method may be readily used for the measurement of the concentration of a luminescent material, or more particularly, a fluorophore in blood. In this case the three fibers may be incorporated into a catheter with the probes spaced apart the appropriate distance at the end of the catheter which is insertable into a blood vessel.

The method of measuring concentration of luminescent materials in turbid media can also be used in non biomedical applications. Several nonlimiting examples include measurement of luminescent or fluorescent materials in bioreactors that typically comprise turbid suspensions of cells and the like; measurement of pigments in paints and concentration of pigments and other labeled ingredients in plastics. The present method may also be used for studying flow processes in turbid media by attaching luminescent/fluorescent labels to species and studying the flow and mixing behavior in the turbid media.

The method has been described using the ratio of fluorescence to reflectance, however it will be understood by those skilled in the art that the this functional form is not meant to be limiting. The relationship of F/R is linear with respect to concentration in many of the examples disclosed herein so that this ratio is the simplest and hence the preferred functional relationship to use. In cases where F/R is non linear, it may be more convenient to use some other functional relationship of expressing the concentration as a function of both the reflectance and fluorescence (i.e. [fluorophore]=f(F,R)). Specifically, functions of the form $F^x/R^y$ wherein x and y can have any value in the range 0 to +infinity. These functions will be directly proportional to the fluorophore concentration. For values of x and y that are less than 0, the function would have properties analogous to those of the function R/F. For these functions, as F goes towards 0, the value of the function would go to infinity, an ineffectual result in terms of determining the concentration of the fluorophore. For cases where x is positive and y is negative, the function would have properties analogous to those of the function RF. Such functions are not capable of correcting for the scattering and absorption properties of the turbid medium. Other functions that contain the function $F^x/R^y$ may also be used, i.e. $g(y)=f(F^x/R^y)$, for example: a $(F^x/R^y)$. Whatever the choice of function f(F, R) being plotted during the measurements the same function is used to prepare the calibration curve wherein $f(F_c, R_c)$ is plotted against concentration of the luminescent/fluorescent compound.

The optimum distances D1 and D2 are obtained by constructing several sample turbid media with known optical properties mimicking the optical properties of the samples for which the concentration measurements are to be made. Fluorescence and reflectance measurements are then performed at several distances from the excitation point for all turbid samples and a best fit to f(F, R) is obtained for each pair of distances. The pairs of distances exhibiting the lowest sum of squares of residuals are preferred for making the measurements since the lower sum of squares of residual values indicates that a measurement of the ratio of the fluorescence to the reflectance at those distances is substantially indicative of the fluorophore concentration in the turbid sample, regardless of the optical properties of the sample. Example 2 discussed hereinafter illustrates the experimental approach to determining the preferred values of D1 and D2.

However, it will be understood by those skilled in the art that D1 and D2 may also be calculated theoretically using a model such as Monte Carlo simulation, numerical solution of the radiation transport equation, or diffusion theory to calculate the fluorescence at a plurality of distances D1 from the source and the reflectance at a plurality of distances D2 from the source for a fixed concentration of fluorophore and for certain values of the absorption and scattering coefficients of the turbid medium. The calculation is repeated for a range of increasing fluorophore concentrations. This is repeated for an effective number of turbid media with an appropriate range of optical properties. For each pair of distances the effective function of both fluorescence and reflectance (f(F, R)) is plotted versus concentration of the luminescent compound for all the reference turbid media and a regression analysis is performed to calculate a best fit function and calculate a correlation coefficient. The pairs of distances D1 and D2 having a sum of squares of residuals lower than a threshold value are selected.

The invention will be further illustrated with the following non-limiting examples.

EXAMPLE 1
Intralipid Phantoms

Several experiments were performed which measured the fluorescence and reflectance of a large variety of phantom solutions with different optical properties. The water-based phantom solutions typically consisted of intralipid as the scatterer, Melan ink as background absorber and one of $AlPcS_4$, or Fluorescein as the fluorescent drug being measured. Intralipid phantoms have been used as tissue-simulating materials for several years by many researchers, see for example "Light scattering in Intralipid 10% in the wavelength range of 400–1100 nm", H. J. van Staveren et al., Applied Optics 30: 4507–4514 (1991). Several baseline intralipid phantoms were made with different absorption and scattering coefficients. To each of these were added known aliquots of the fluorescent drug prior to reflectance and fluorescence measurements.

The apparatus consisted of a diffuse reflectance and fluorescence probe, spectrometer, and CCD imaging system. In these experiments, the baseline optical properties of the liquid intralipid phantoms were determined using the general diffuse reflectance technique of Patterson et al. disclosed in T. J. Farrell, M. S. Patterson, and B. C. Wilson "A diffusion theory model of spatially resolved steady state diffuse reflectance for the noninvasive determination of tissue optical properties in vivo", Med. Phys. Vol 19, pp 879–888 (1992); M. S. Patterson, J. E. Haywoard, T. J. Farrell, and B. C. Wilson "A general purpose instrument for PDT dosimetry" SPIE Proc. 2371, pp 477–481. (1995); and R. A. Weersink, J. E. Hayward, K. R. Diamond and M. S. Patterson "Accuracy of non-invasive in vivo measurements of photosensitizer uptake based on a diffusion model of reflectance spectroscopy." Photochem. Photobiol. Vol 66 pp 326–335 (1997). The probe consisted of a source, and 8 collection fibers located 0.86 to 10 mm from the source fiber along the circumference of a 10 mm circle. At the spectrometer entrance, the collection fibers were equally spaced parallel to the entrance slit axis. The spectrometer disperses the light from each fiber onto the CCD detector. One exposure of the CCD therefore provides spectra of light collected at eight distances over a range of 300 nm with a resolution of 2 nm.

Fluorescence measurements were made by replacing the broad band QTH lamp as the light source with a laser at an appropriate wavelength for the excitation of the drug being studied. This included an Argon ion laser and dye laser pumped by this laser, as well as a 630 nm diode laser. Fluorescence was measured at 0.86 mm from the source (D1 in FIG. 1), and the reflectance of the excitation light collected at 1.42 mm from the source (D2 in FIG. 1).

Analysis of the fluorescence data consisted of a calculation of the ratio of fluorescence measured at one wavelength at 0.86 mm from the source over the excitation light measured at 1.42 mm. This ratio was plotted with respect to the known concentration of the drug, based on the aliquots added. These plots for phantoms of differing baseline optical properties were then combined and differences between baseline phantom measurements assessed.

Several factors were studied including optimal distances where the ratio of fluorescence/reflectance is constant for a variety of background optical properties; level of accuracy that can be achieved, linearity of the ratio with respect to drug concentration; and performance for different fluorescent drugs.

The optimal distances found were 0.86 mm for the fluorescence fiber and 1.42 mm for the reflectance fiber. Other pairs of distances were tried, but with less success as will be described in examples below.

The plots in FIGS. 3a, 3b, 4a and 4b depict measurements using different fluorescent molecules in phantoms with a variety of optical properties. For each graph, the experimental configuration was constant. Only the optical properties of the phantom and the drug concentration in the phantom were changed. The ratio of the fluorescence measured at 0.86 mm over the reflectance measured at 1.42 mm is plotted with respect to drug concentration. In each graph, several of these "ratio vs. concentration" plots are shown for phantoms of different background optical properties.

Figure 3A:
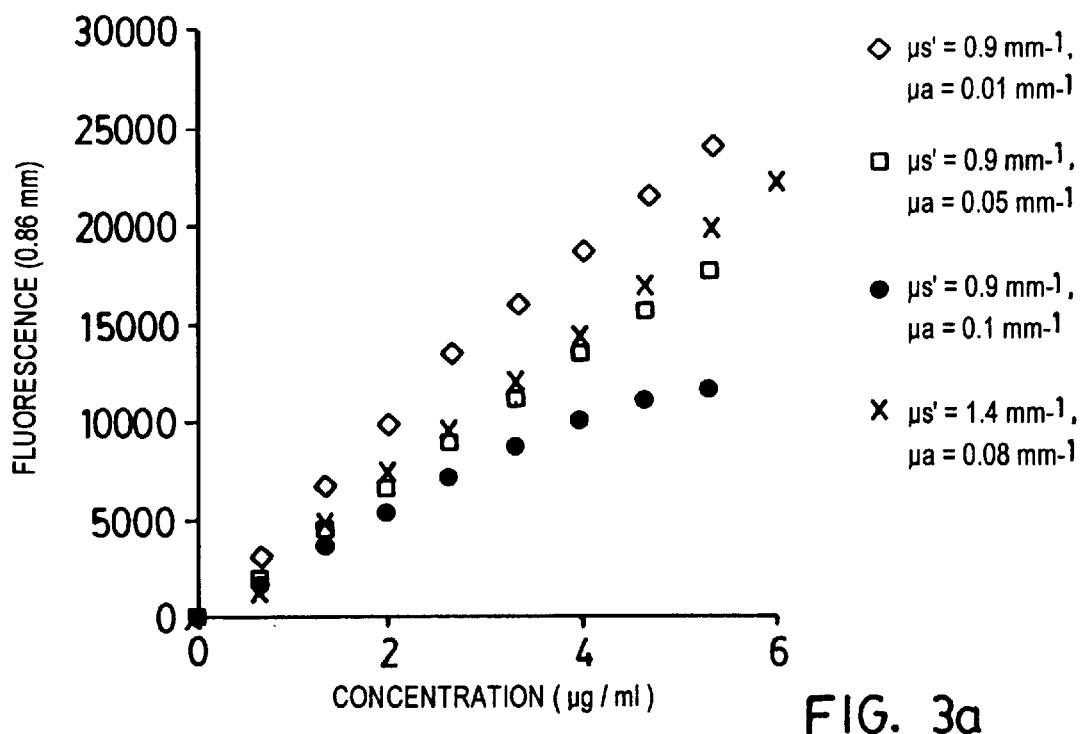
FIG. 3a shows the raw fluorescence signal for various concentrations of $AlPcS_4$ measured in a series of turbid solutions of different optical properties with the fluorescence being excited at 670 nm and measured at 720 nm a distance of 0.86 mm from the source fiber.
Figure 3B:
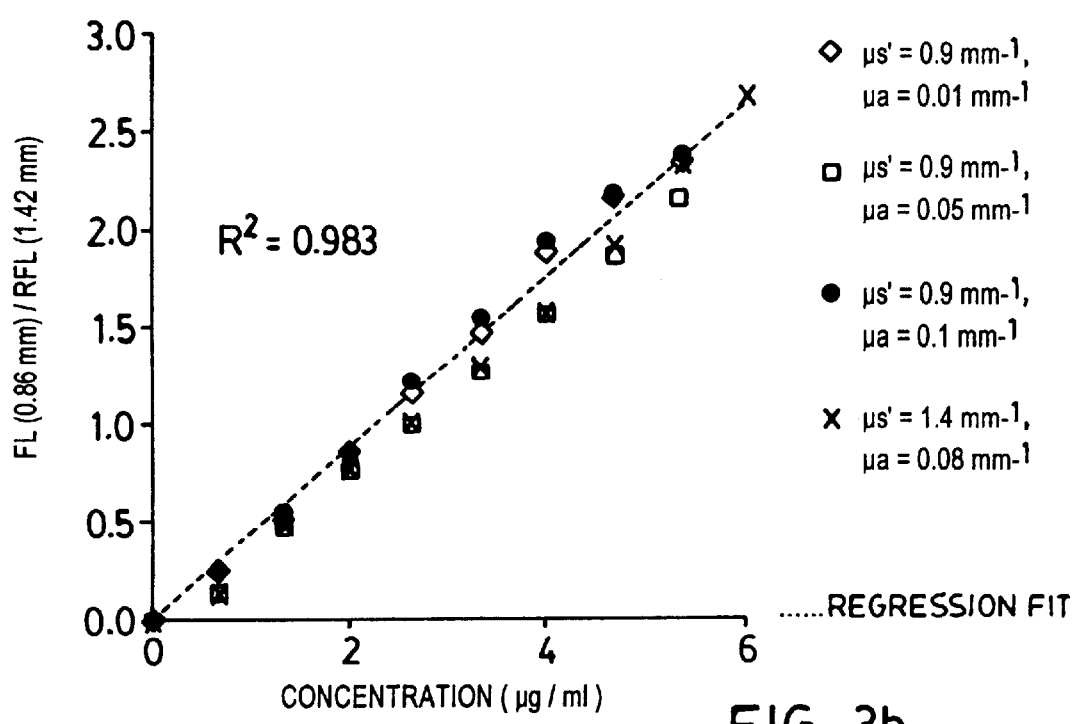
FIG. 3b is a plot of the ratio of the fluorescence of $AlPcS_4$ measured at 0.86 mm from FIG. 3a to the reflectance of the excitation light measured at 1.42 mm versus the drug concentration.

In the plots of FIG. 3a, $AIPcS_4$ is excited at 670 nm, with fluorescence measured at 720 nm. FIG. 3a shows the raw fluorescence signal (i.e. uncorrected by the excitation measurement) for a range of background optical properties. Here it can be seen that the signal strongly depends on the optical properties of the phantom so that a calibration curve could not be used for a range of tissues or for a single tissue where the optical properties might change over time (due to blood flow or oxygenation, for example). The plot in FIG. 3b depicts the ratio of the fluorescence measured at 0.86 mm to the reflectance of the excitation light measured at 1.42 mm versus the drug concentration. Note that data points from different phantom solutions fit on almost the same line. As can be observed in the graph of FIG. 3b, the fluorescence/reflectance ratio is essentially constant for a constant fluorophore concentration in "tissues" of different optical properties. These data can be used to construct a calibration curve for use on tissue with unknown optical properties.

A quantitative measurement of the $AIPcS_4$ uptake in a patient could then be taken using the same equipment as used in these measurements. For instance, measuring a ratio of 1.7 with this apparatus would lead to the conclusion that the in vivo drug uptake was 4.0 $\mu g/g$ of tissue. If different excitation sources, spectrometers, etc. are used, then a different ratio of the fluorescence to excitation will be measured for tissue uptake of 4.0 $\mu g/g$. But by providing a calibration phantom, different instruments could be calibrated to this phantom to provide a new appropriate calibration curve.

Figure 4A:
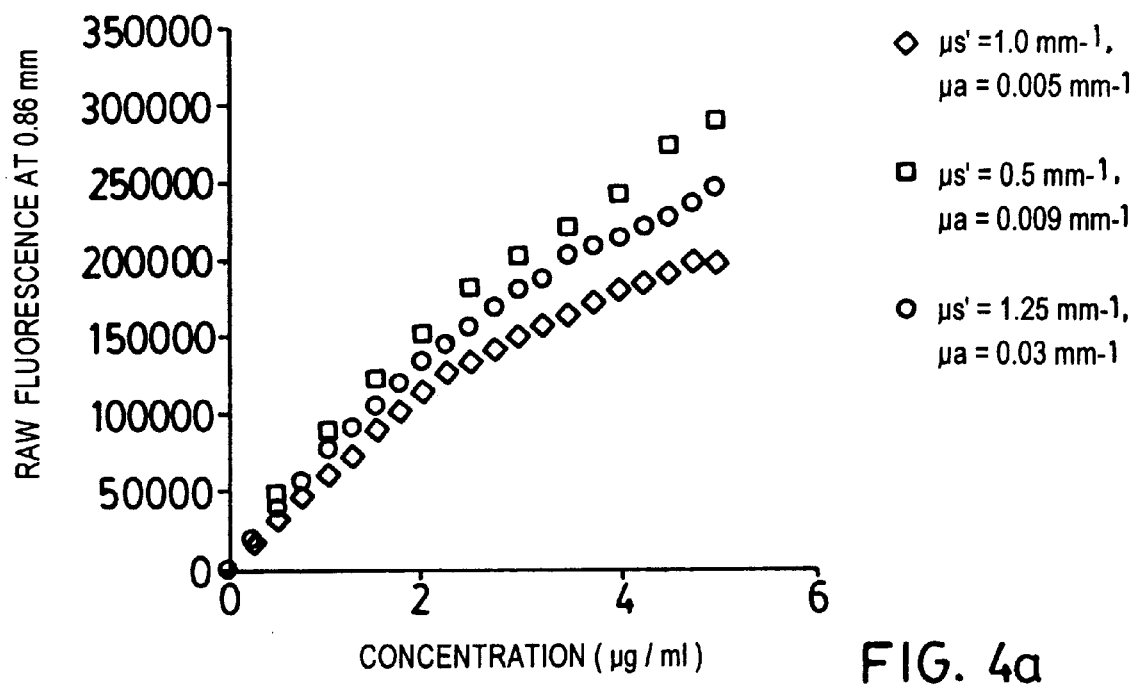
FIG. 4a is a plot of the raw fluorescence signal for fluorescein excited at 488 nm, with fluorescence measured at 530 nm a distance of 0.86 mm from the source fiber.
Figure 4B:
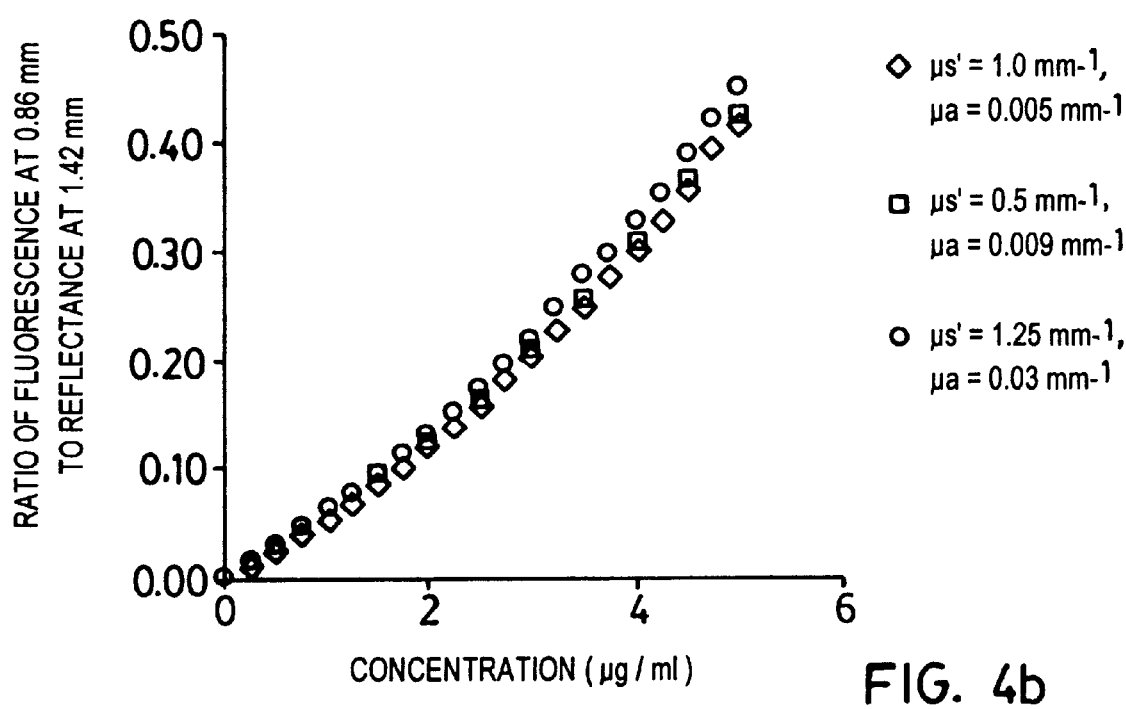
FIG. 4b is a plot of the ratio of fluorescence of fluorescein measured at 0.86 mm from FIG. 4a to the reflectance of the excitation light measured at 1.42 mm versus the fluorescein concentration.

Similar graphs are shown for fluorescein in intralipid phantoms in FIGS. 4a and 4b. The graphs depict essentially the same results as the $AIPcS_4$ phantoms. The method has a precision of better than 10%. The line of the ratio versus concentration in FIG. 3b is almost linear for the $AIPcS_4$ phantoms, but curves upwards for the Fluorescein phantoms, see FIG. 4b. This depends to a large degree on the amount of reabsorption of the fluorescence by the drug. This can be significantly reduced or minimized by the choice of wavelength for fluorescence detection. Even if the curve is nonlinear, it is useful nevertheless. If the plot of F/R is linear, calibration only needs to be made at single concentration point. Simple arithmetic can then be used to quantify the fluorophore concentration of the sample being measured. If the plot of F/R is nonlinear, then calibration needs to be made over the whole range of concentration values to be measured. In this case, a simple look-up table is sufficient for quantifying the fluorophore concentration of the measured sample.

EXAMPLE 2

Comparison of Distance Pairs using Intralipid Phantoms

A further series of intralipid phantom measurements were made with the intent of determining the optimal pair of distances to be used in the fluorescence/reflectance ratio. As described above, a series of liquid phantoms was prepared using intralipid as the scatterer and Melan ink as the absorber. The optical properties of the phantoms were determined using spatially resolved diffuse reflectance. Several phantoms of different optical properties (reduced scattering and absorption) were prepared. To each, the fluorophore $AIPcS_4$ was added in known aliquots so as to increase the concentration of the fluorophore in the phantom. At each aliquot addition, a measurement was taken of the reflectance and fluorescence at several distances (0.86 mm to 3.4 mm respectively).

The ratio of fluorescence to reflectance was calculated for all twenty-five combinations of distances. For example, the ratio of fluorescence to reflectance was calculated for fluorescence at 0.86 mm to reflectance at 0.86 mm, 1.42 mm, 1.92 mm, 2.38 mm and 3.4 mm. This procedure was repeated for fluorescence measured at 1.42 mm, 1.92 mm, 2.38 mm and 3.4 mm from the source fiber. This measurement and calculation was performed for four sets of phantoms, each with different background optical properties.

Figure 5A:
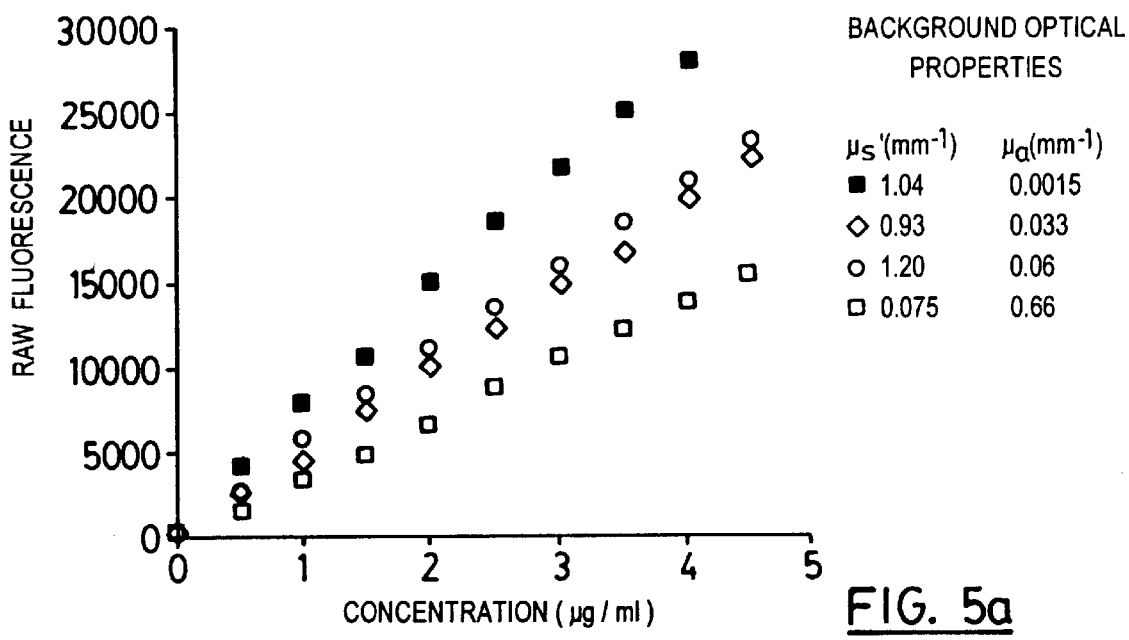
FIG. 5a is a plot of the raw fluorescence of $AlPcS_4$ measured at 750 nm excited at 633 nm versus concentration of $AlPcS_4$.
Figure 5B:
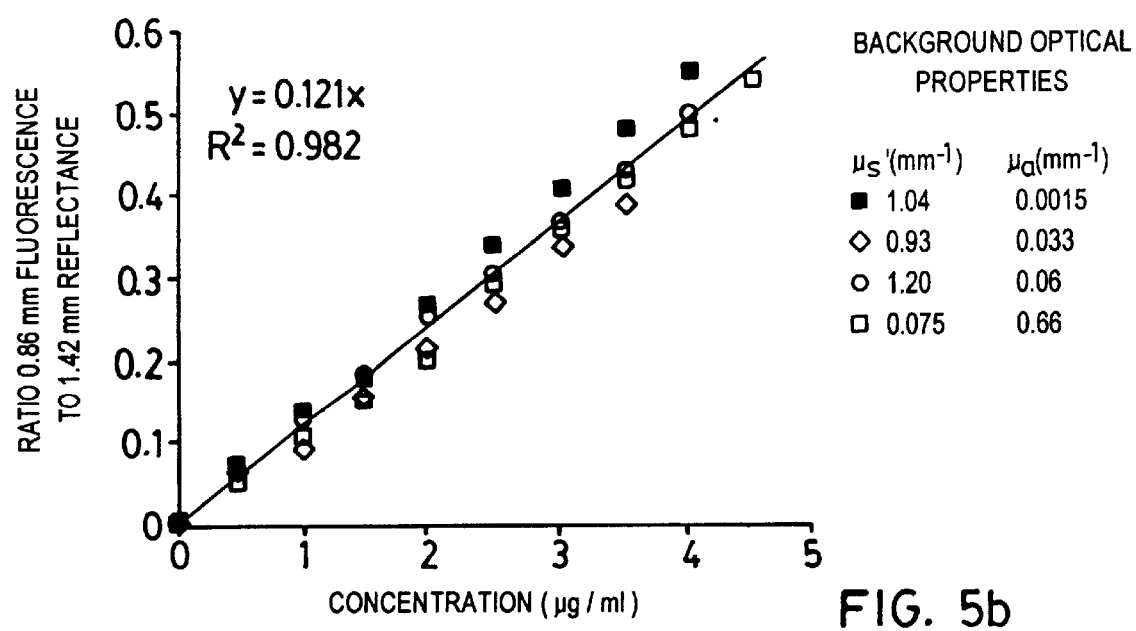
FIG. 5b is a plot of the ratio of fluorescence of $AlPcS_4$ collected at 0.86 mm (depicted in FIG. 5a) to reflectance collected at 1.42 mm versus $AlPcS_4$ concentration, the reflectance measured at the excitation wavelength, 633 nm.
Figure 6A:
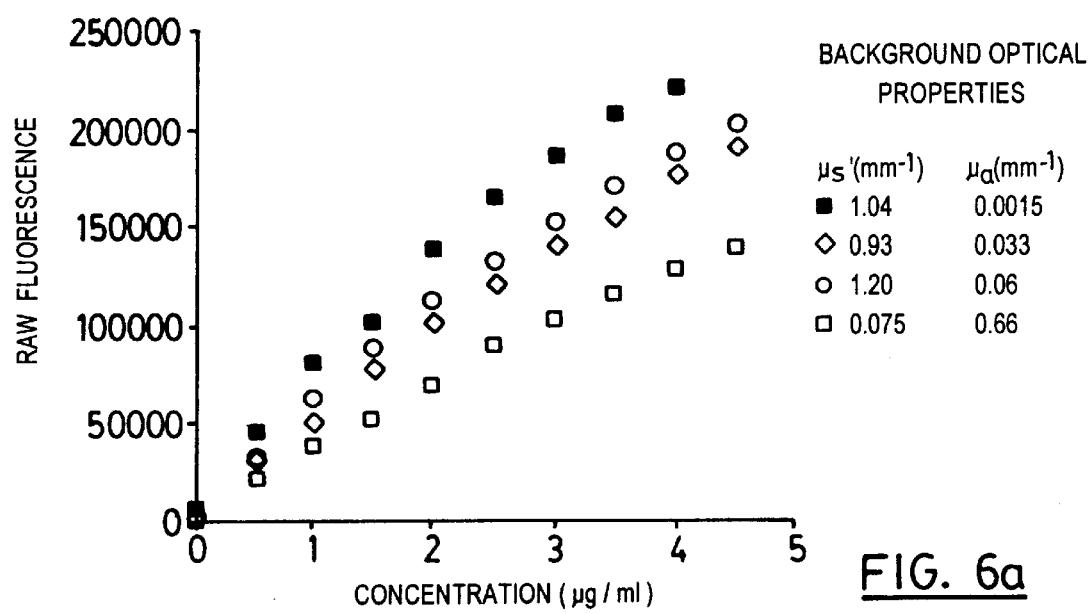
FIG. 6a is a plot of the raw fluorescence of $AlPcS_4$ in a series of turbid solutions measured at 680 nm excited at 633 nm versus concentration of $AlPcS_4$.
Figure 6B:
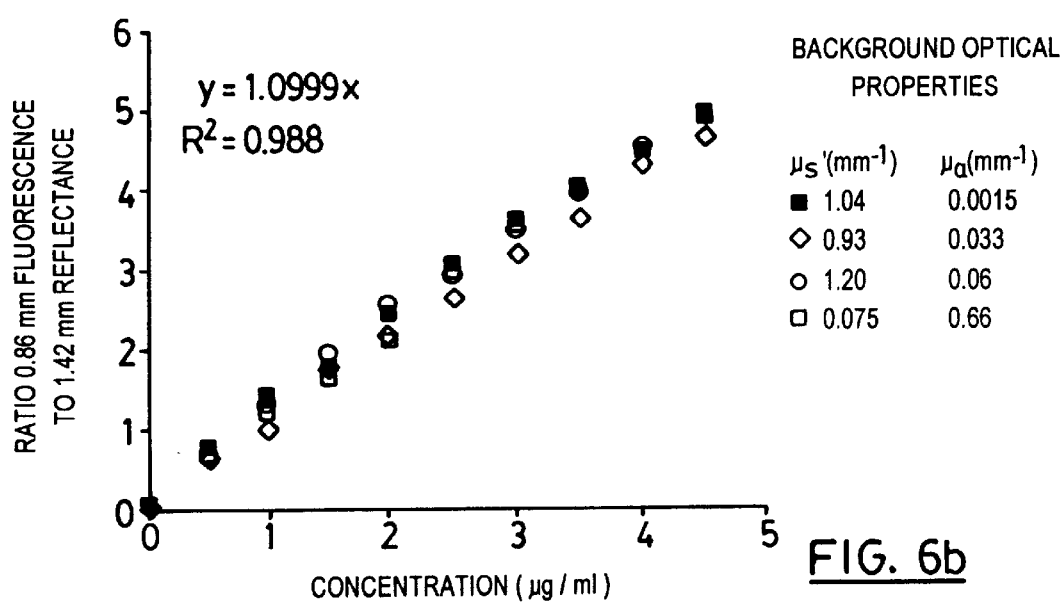
FIG. 6b is a plot of the ratio of fluorescence of $AlPcS_4$ collected at 0.86 mm (depicted in FIG. 6a) to reflectance collected at 1.42 mm versus $AlPcS_4$ concentration, the reflectance measured at the excitation wavelength, 633 nm.

For each particular fluorescence/reflectance ratio, linear regression was performed for the fluorescence/reflectance ratio versus fluorophore concentration. For example, FIG. 5a shows the raw fluorescence at 750 nm collected at 0.86 mm for the 4 different phantoms measured. Note that the fluorescence at each concentration varies substantially depending on the background optical properties. FIG. 5b is the same set of measurements, but it depicts the ratio of the fluorescence at 0.86 mm to the reflectance at 1.42 mm. A linear regression of this data gives an $R^2$ value of 0.9822. Such a high correlation indicates that a measurement of the ratio of the fluorescence at 0.86 mm to the reflectance at 1.42 mm is substantially indicative of the fluorophore concentration in the turbid sample, regardless of the optical properties of the sample. FIG. 6a shows the raw fluorescence at 680 nm collected at 0.86 mm for the 4 different phantoms measured. FIG. 6b is the same set of measurements, but it depicts the ratio of the fluorescence at 0.86 mm to the reflectance at 1.42 mm. A linear regression of this data gives an $R^2$ value of 0.988.

Tables 1 and 2 give the $R^2$ values for all sets of distance pairs for the fluorescence measured at 680 nm and 750 nm. For both fluorescence wavelengths, the optimal pair of distances is fluorescence at 0.86 mm and reflectance at 1.42 mm. The set of background optical properties used in these experiments is typical of the optical properties measured for tissue.

EXAMPLE 3
Effect of Background Absorption of the Turbid Medium on the Ratio of Fluorescence to Reflectance The choice of the optimal pair of distances to be used in the measurement of the ratio of fluorescence to reflectance was further examined by studying the effect of background absorption on the measured ratio. A liquid phantom with a fixed reduced scattering value and a fixed concentration of fluorophore was prepared. Measurements of the phantom optical properties were made at the fluorescence emission wavelength (750 nm) using spatially resolved diffuse reflectance. Measurements of the reflectance of the excitation light and fluorescence were made at both 0.86 mm and 1.42 mm since these distances produced the highest correlations in the previous set of experiments. The background absorption was increased by adding aliquots of Melan ink. The background optical properties were measured and the reflectance and fluorescence measurements were repeated. This procedure was repeated so that a large variation in the background absorption coefficient was examined.

Figure 7A:
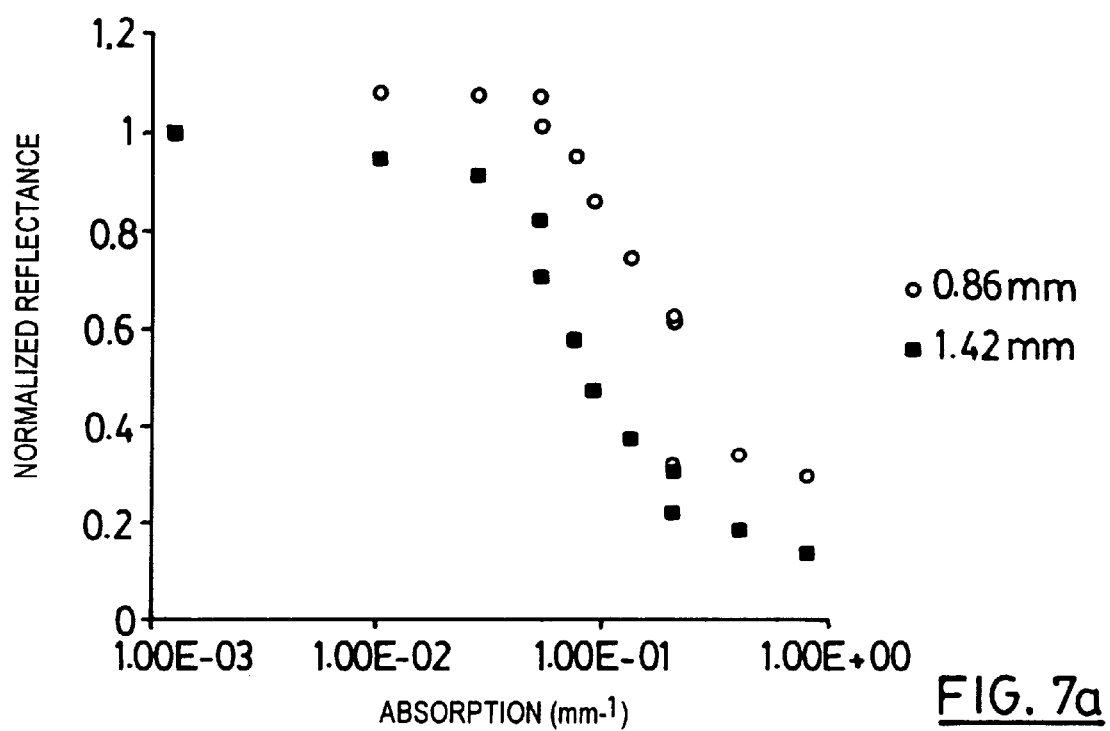
FIG. 7a is a plot of the normalized reflectance collected at 0.86mm and 1.42 mm from the source fiber versus the background absorption coefficient, the reflectance measured at the excitation wavelength, 633 nm.
Figure 7B:
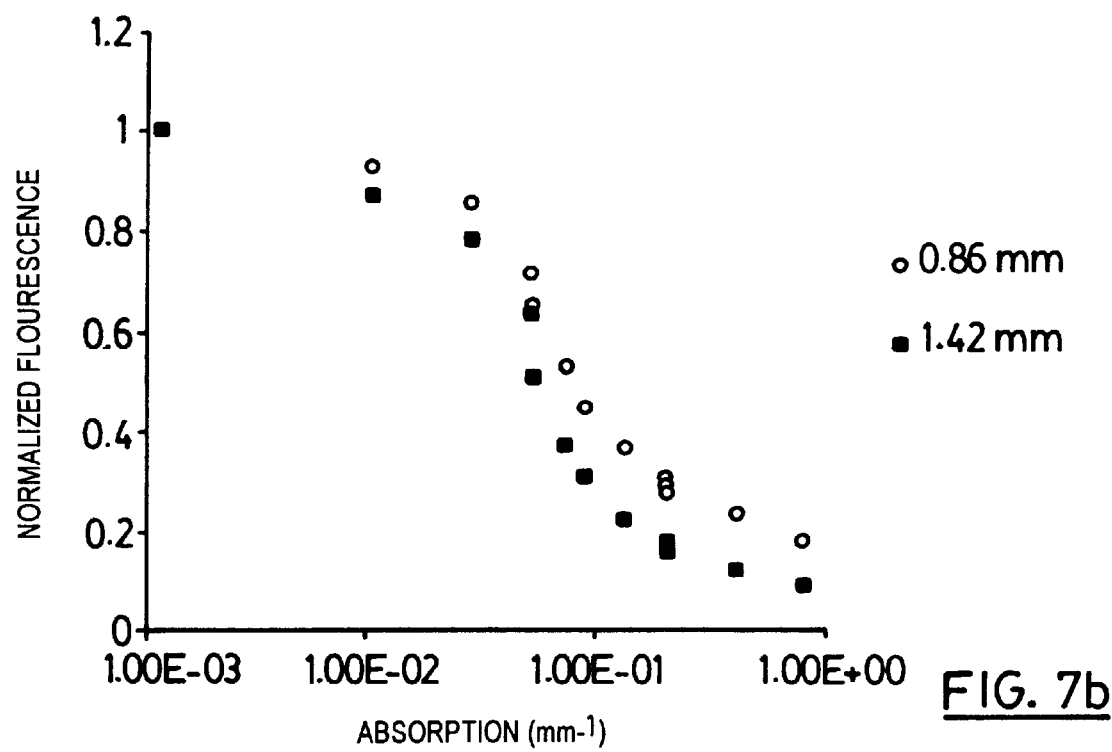
FIG. 7b is a plot of the normalized $AlPcS_4$ fluorescence collected at 0.86 mm and 1.42 mm from the source fiber versus the background absorption coefficient of the turbid medium, the fluorescence measured at 750 nm.

FIG. 7a shows the normalized reflectance measured at 0.86 mm and 1.42 mm from the source fiber for a range of absorption coefficients from 0.001–1.0 mm$^{-1}$. FIG. 6b shows the normalized fluorescence measured at 0.86 mm and 1.42 mm from the source fiber over absorption coefficients of 0.001–1.0 mm$^{-1}$. The reduced scattering coefficient was equal to 1.0 mm$^{-1}$ and the AlPcS$_4$ concentration was 1 µg/ml. In both graphs, it is evident that the measured signal drops substantially with increased background absorption. It is also apparent that the changes in reflectance and fluorescence signals are different at the two measurement distances.

Figure 8:
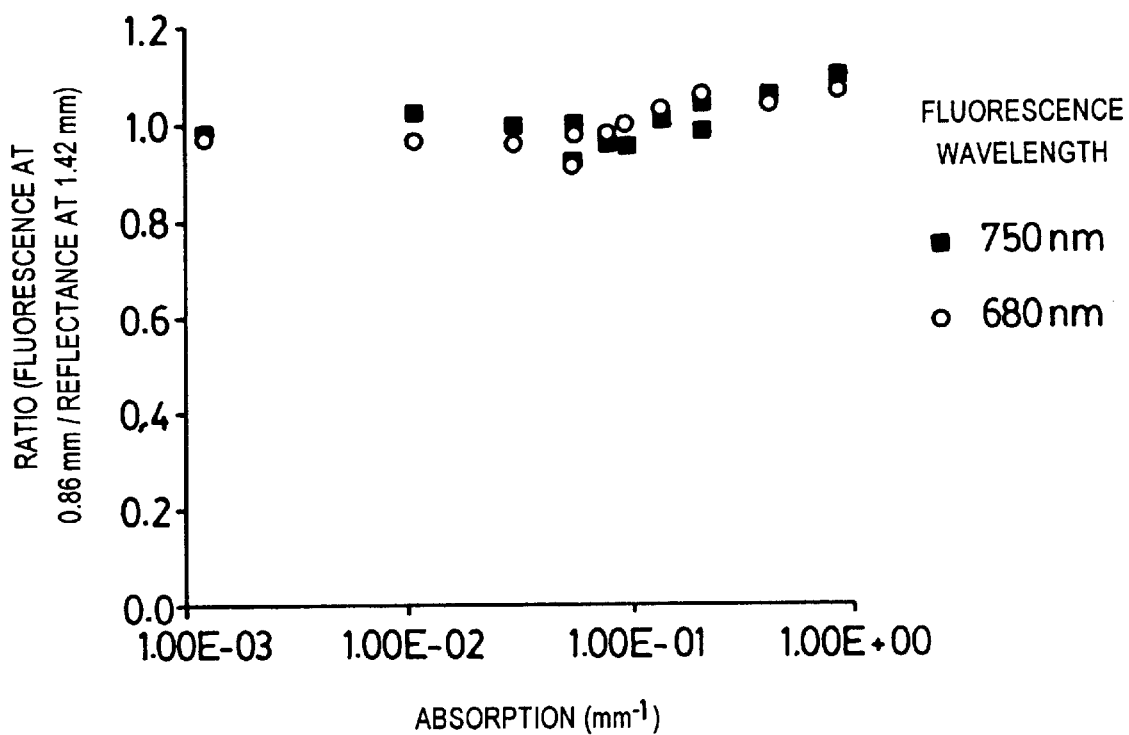
FIG. 8 is a plot of the measured fluorescence/reflectance ratio of $AlPcS_4$ versus background absorption of the turbid medium, the fluorescence was measured at 750 nm and collected at 0.86 mm and the reflectance was measured at 633 nm and collected at 1.42 mm.
Figure 9A:
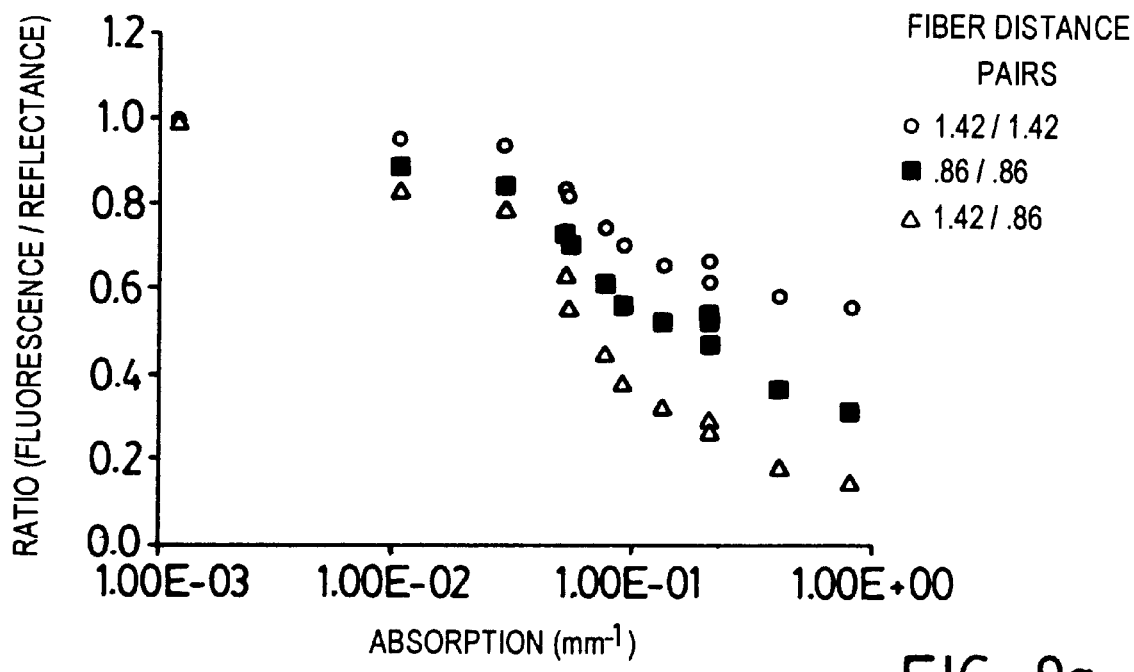
FIG. 9a is a plot of the measured fluorescence/reflectance ratio for $AlPcS_4$ versus background absorption of the turbid medium for other possible pairs of fluorescence and reflectance collection distances, the fluorescence was measured at 680 nm and the reflectance was measured at 633 nm.
Figure 9B:
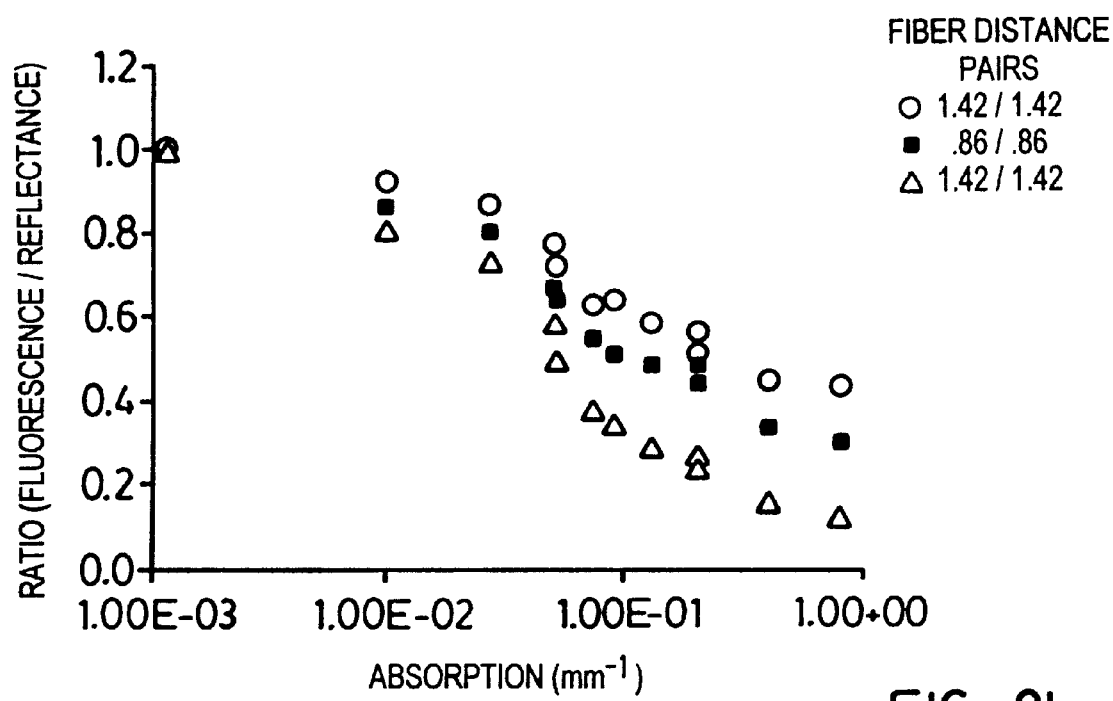
FIG. 9b is a plot of the measured fluorescence/reflectance ratio for $AlPcS_4$ versus background absorption of the turbid medium for other possible pairs of fluorescence and reflectance collection distances, the fluorescence was measured at 750 nm and the reflectance was measured at 633 nm.

FIG. 8 shows the ratio of the fluorescence measured at 0.86 mm to the reflectance measured at 1.42 mm for both 750 nm and 680 nm versus background absorption. Clearly, the ratio remains the same across the large range of background absorption values, indicating that for a fixed concentration of fluorophore, the ratio of fluorescence to reflectance with this pair of distances is constant, despite large changes in background absorption. In FIG. 8, the ratio of fluorescence to reflectance versus absorption is shown for the other possible distance combinations. For these other distance pair combinations, the ratio changes significantly with increasing absorption, even though the concentration of fluorophore remains constant.

EXAMPLE 4
Effect of Reduced Scattering on the Ratio of Fluorescence to Reflectance The choice of the optimal pair of distances to be used in the measurement of the ratio of fluorescence to reflectance was further examined by studying the effect of reduced scattering on the measured ratio. A liquid phantom with a fixed background absorption value, $\mu_a$=0.005 mm$^{-1}$, a fixed concentration of fluorophore ([AlPcS$_4$]=1.0 µg/ml) and low reduced scattering was prepared. Measurements of the phantom optical properties were made at the fluorescence emission wavelength (750 nm) using spatially resolved diffuse reflectance. Measurements were made of the reflectance of the excitation light and the fluorescence at both 0.86 mm and 1.42 mm. The reduced scattering coefficient was increased by adding aliquots of intralipid to the phantom. The background optical properties of the phantom were measured and the reflectance and fluorescence measurements were repeated. This procedure was repeated so that a large variation in reduced scattering values was examined. The range of typical tissue reduced scattering values ($\mu_s'$=0.5 mm$^{-1}$ to 1.5 mm$^{-1}$) was examined.

Figure 10:
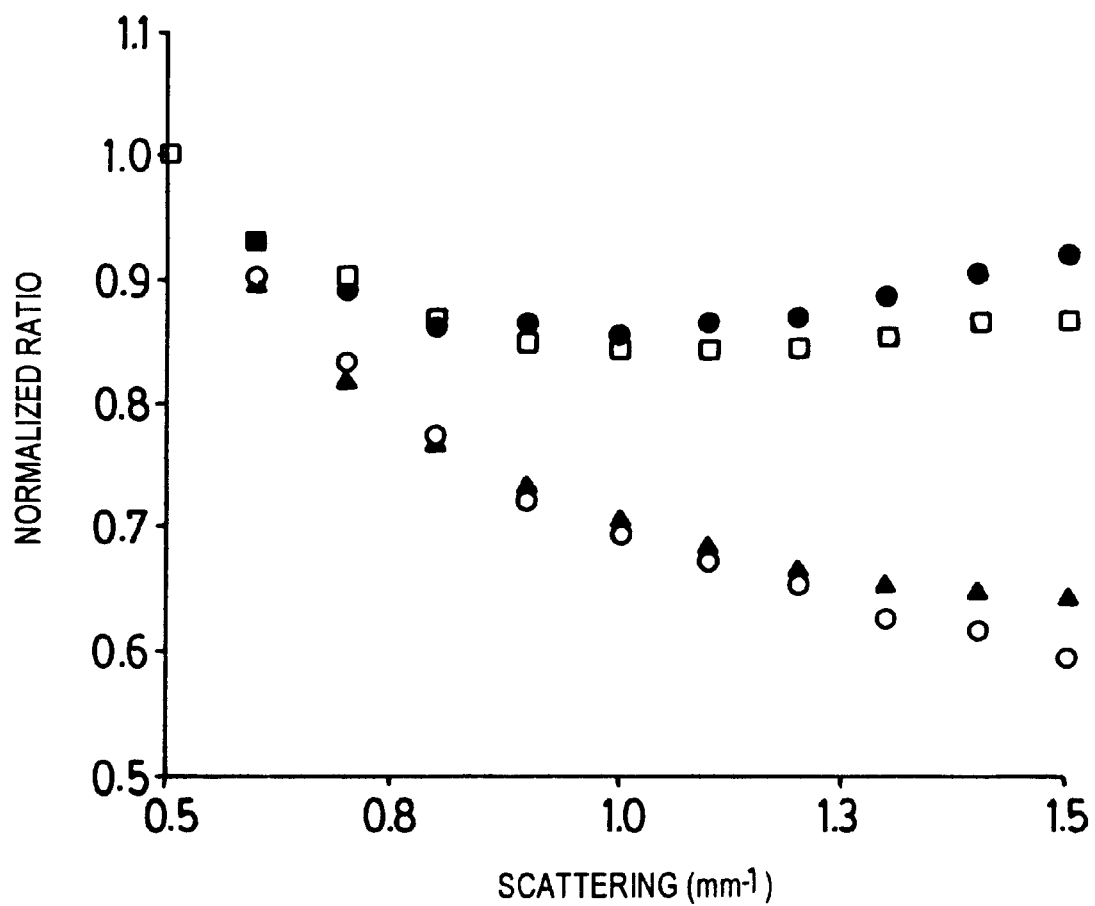
FIG. 10 is a plot of the measured fluorescence/reflectance ratio $AlPcS_4$ versus reduced scattering coefficient of the turbid medium for several combinations of fluorescence distance and reflectance collection distances with the fluorescence measured at 750 nm and reflectance measured at 633 nm, the concentration of $AlPcS_4$ was 1 $\mu$g/ml and background absorption of the turbid medium was 0.005 $mm^{-1}$.

FIG. 10 shows the fluorescence/reflectance ratios for several combinations of fiber distances. The combinations that give the smallest change with increased reduced scatter are 0.86/1.42 and 1.42/1.42, both with standard deviations of only 5% or less. For the range of reduced scattering values measured, the pair at 0.86/1.42 has a slightly smaller standard deviation than the collection pair at 1.42/1.42, although it is uncertain if the differences in the standard deviations for these two sets of data is statistically significant.

Example 3 demonstrates that the selection of the correct collection distances is important in reducing the effects of scattering on the F/R measurement, although this selection may not be unique. For the preferred pair of collection distances for this system (0.86 mm for fluorescence and 1.42 mm for reflectance) the measured F/R has a smaller standard deviation across the range of physiologically important tissue scattering values than most other combinations measured. When the results of Examples 2 and 3 are examined together, it is apparent that the preferred ranges for collection distances D1 and D2 disclosed herein are unique in that the ratio F/R is a constant for constant fluorophore concentration, regardless of the background absorption and scattering values.

EXAMPLE 5
In Vivo Test

In one in vivo study, a rabbit was injected with AlPcS$_4$ at a dose of 3 mg/kg and measurements taken 24 hours later. Measurements of the fluorescence and reflectance were taken on the back skin, the underlying muscle and, ex vivo, on the liver. These tissue types were chosen because of their large range of optical properties. The measured tissue was excised and the drug uptake determined by fluorescence assay as described in L. Lilge, C. O'Carroll and B. C. Wilson "Photosensitizer quantification for ex vivo tissue samples: a tissue solubilization technique", J. Photochem. Photobiol. B, Vol 39 pp 229–235 (1997). A set of calibration measurements on intralipid phantoms were also taken to correlate the measured ratio with concentration. FIG. 10 depicts a plot of concentrations determined by the non-invasive fluorescence technique versus the concentration determined by fluorescence assay. The line is reasonably straight ($R^2=0.93$), with a slope of 0.87. The non-invasive fluorescence technique underestimates the concentration by about 13%, but the relationship is linear, indicating that with improvements in calibration methods, the non-invasive technique can accurately determine the in vivo drug concentration.

Figure 11:
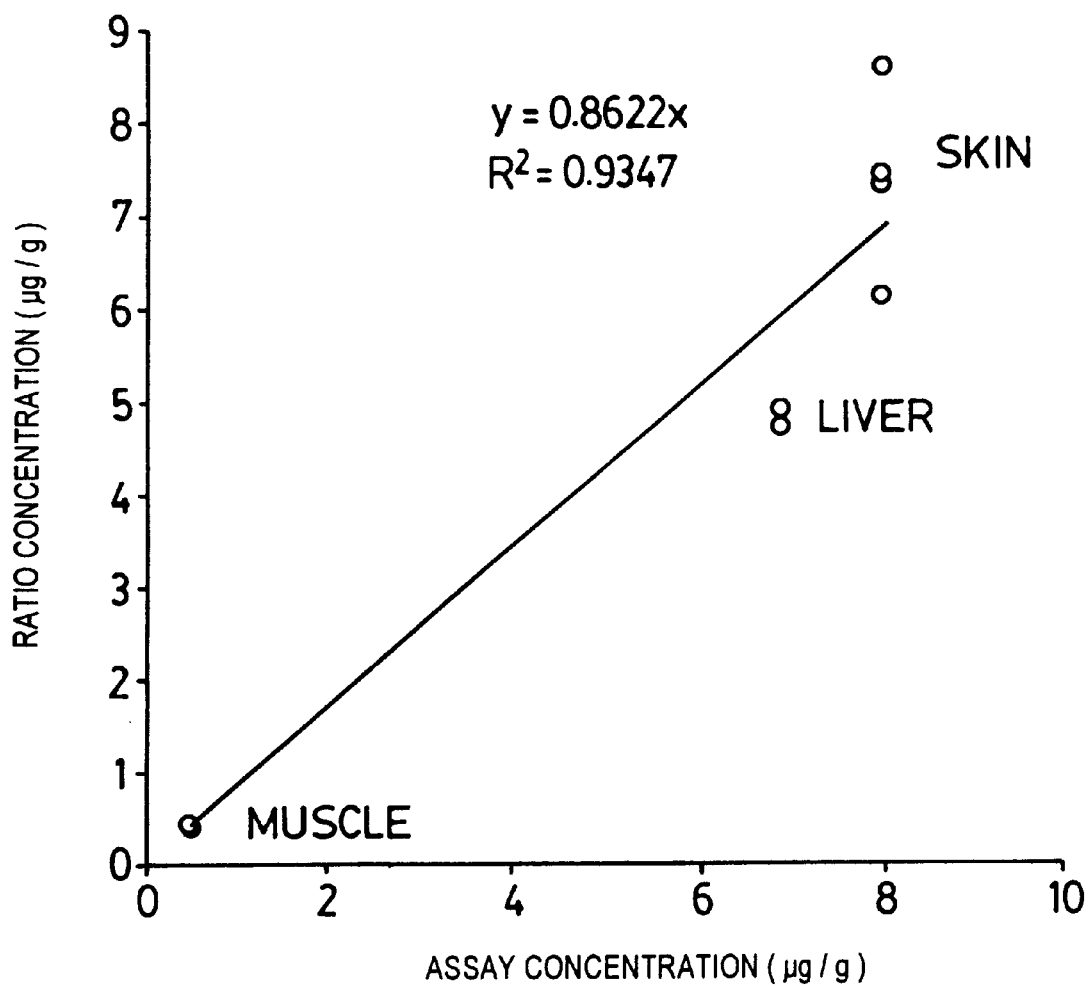
FIG. 11 is a plot of concentrations determined by the non-invasive fluorescence technique versus the concentration determined by fluorescence assay in three different tissue types for a rabbit injected with $AlPcS_4$.
Figure 12A:
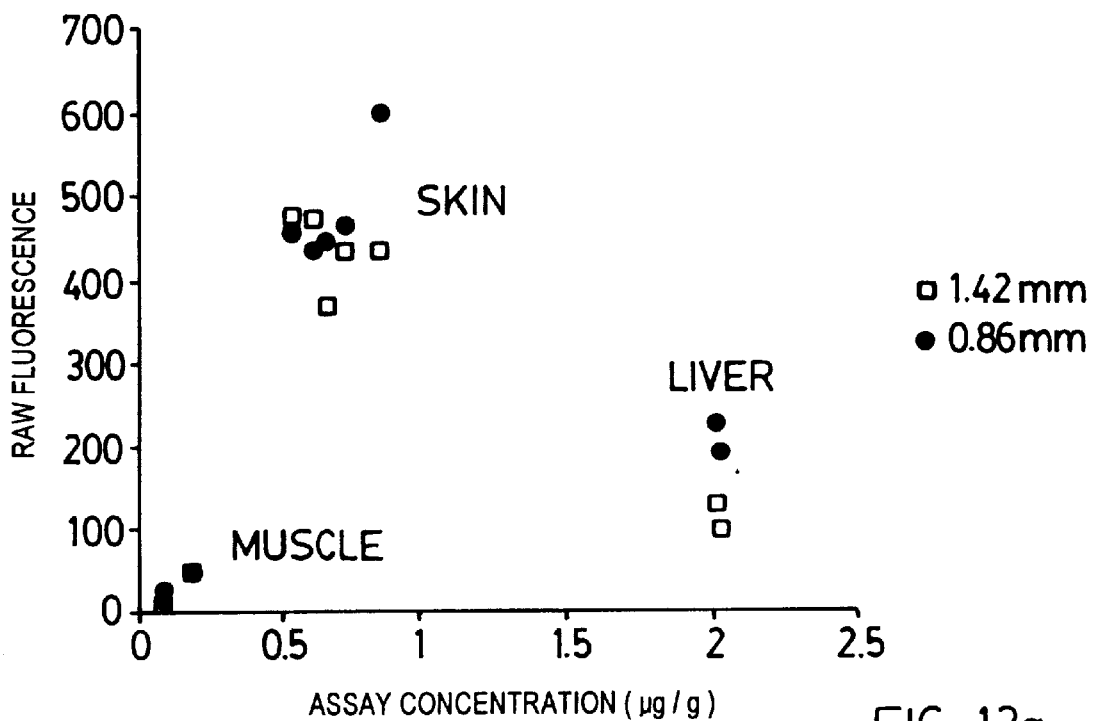
FIG. 12a is a plot of the raw fluorescence at 750 nm collected at both 0.86 mm and 1.42 mm for a rabbit injected with $AlPcS_4$.
Figure 12B:
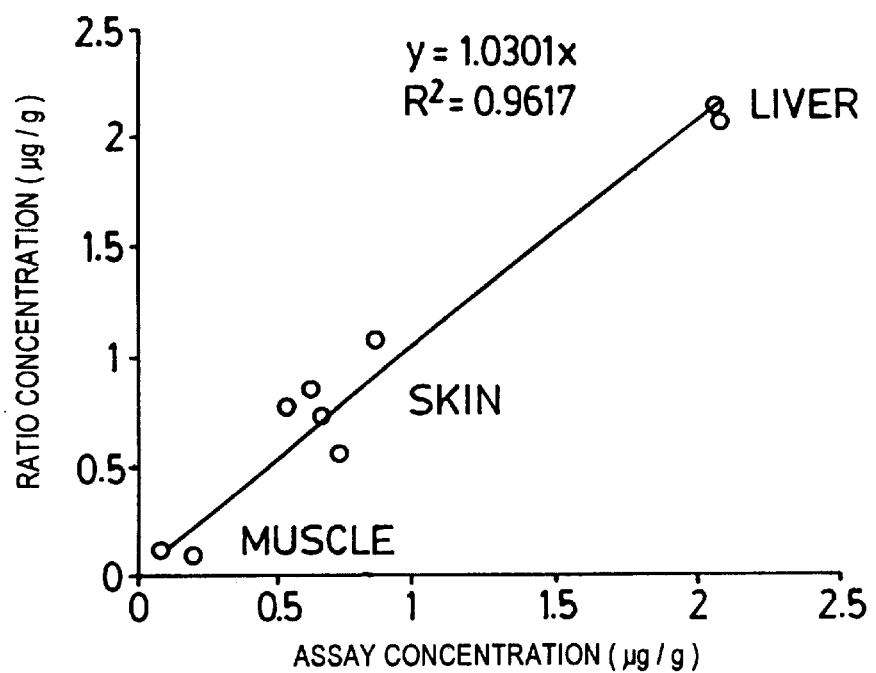
FIG. 12b is a plot of the ratio of fluorescence $AlPcS_4$ collected at 0.86 mm from FIG. 10a to the reflectance of the excitation light collected at 1.42 mm versus the $AlPcS_4$ concentration as determined by tissue assay with the fluorescence measured at 750 nm and the reflectance measured at the excitation wavelength, 633 nm.

In a second in vivo experiment, a rabbit was injected with $AlPcS_4$ at a dose of 1.5 mg/kg and measurements taken 24 hours later. Measurements were taken on several locations on the skin, and muscle of the rabbit, as well as two positions on the liver. In total, ten tissue locations were measured with small tissue samples excised at these locations for drug uptake assays. The set of calibration curves for this in vivo measurement is shown in FIGS. 3a and 3b. FIGS. 11a shows the raw fluorescence measured at both 0.86 mm and 1.42 mm and the ratio of fluorescence measured at 0.86 mm to the reflected excitation light at 1.42 mm is shown in FIG. 6b. The raw fluorescence measured on the skin is more than twice that measured on the liver, even though the in vivo concentration in the liver is twice that of the skin. The much lower fluorescence signal measured in the liver tissue is due to its much higher absorption coefficient than in skin. Clearly, relying on the fluorescence signal alone gives an inaccurate assessment of the in vivo drug concentration, since the different optical properties of different tissue types affects the amount of fluorescent light reaching the tissue surface.

In contrast, the ratio of fluorescence at 0.86 mm to the reflected excitation light measured at 1.42 mm is linear with respect to the in vivo drug concentration, regardless of the tissue optical properties. Comparing the ratios measured on the tissue with those determined in the calibration measurements (FIGS. 3a and 3b) indicate that in this experiment, the present new technique accurately estimates the actual tissue concentration and provides an accurate measurement of the in vivo concentration.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

TABLE 1

Correlations of measured ratio to concentration for several fluorescence/reflectance distance pairs (mm). Fluorescence measure at 680 nm, reflectance measured at 633 nm.

| Reflection Distance | Fluorescence Distance | | | | |
|---|---|---|---|---|---|
| | 0.86 | 1.41 | 1.92 | 2.38 | 3.4 |
| 0.86 | 0.958 | 0.893 | 0.803 | 0.713 | 0.890 |
| 1.41 | 0.988 | 0.892 | 0.828 | 0.828 | 0.611 |
| 1.92 | 0.953 | 0.957 | 0.942 | 0.899 | 0.724 |
| 2.38 | 0.91 | 0.934 | 0.937 | 0.916 | 0.767 |
| 3.4 | 0.779 | 0.819 | 0.877 | 0.896 | 0.874 |

TABLE 2

Correlations of measured ratio to concentration for several fluorescence/reflectance distance pairs (mm). Fluorescence measured at 75 nm, reflectance measured at 633 nm.

| Reflection Distance | Fluorescence Distance | | | | |
|---|---|---|---|---|---|
| | 0.86 | 1.42 | 1.92 | 2.38 | 3.40 |
| 0.86 | 0.967 | 0.923 | 0.850 | 0.797 | 0.619 |
| 1.42 | 0.982 | 0.953 | 0.891 | 0.845 | 0.671 |
| 1.92 | 0.961 | 0.960 | 0.935 | 0.905 | 0.755 |
| 2.38 | 0.923 | 0.931 | 0.919 | 0.900 | 0.768 |
| 3.40 | 0.803 | 0.838 | 0.875 | 0.888 | 0.848 |

Therefore what is claimed is:

1. A method of measuring concentration of a luminescent compound in a turbid medium, comprising:

illuminating a turbid medium with a beam of light having an effective wavelength $\lambda_1$ to excite luminescence in a luminescent compound being detected in the turbid medium;

measuring a luminescence signal F an effective distance of about D1 from the beam of light;

measuring a reflectance signal R at wavelength $\lambda_1$ an effective distance of about D2 from the beam of light wherein the distances D1 and D2 are selected to reduce effects of scattering and absorption variations between turbid samples; and processing the measured R and F signals to produce an effective function f(F, R) and comparing f(F, R) to a calibration curve of $f_c(F_c, R_c)$ versus concentration of the luminescent compound in a turbid medium to determine a concentration of the luminescent compound.

2. The method according to claim 1 wherein the distances D1 and D2 are measured perpendicular from a longitudinal axis of said beam of light.

3. The method according to claim 1 wherein the calibration curve of $f_c(F_c, R_c)$ versus concentration of the luminescent compound is determined for a turbid medium by measuring a calibration luminescence signal $F_c$ at D1 and a calibration reflectance signal $R_c$ at D2 for a plurality of known concentrations of the luminescent compound and plotting the effective function $f_c(F_c, R_c)$ versus concentration of the luminescent compound.

4. The method according to claim 3 wherein the effective function $f(F, R)=F^x/R^y$, where x and y can have any value in a range $0<x$, $y \leq +\infty$.

5. The method according to claim 4 wherein $x=y=1$ such that $f(F, R)=F/R$.

6. The method according to claim 3 wherein $x=y=\frac{1}{2}$ such that $f(F, R)=(F/R)^{0.5}$.

7. The method according to claim 3 wherein the luminescent compound is a fluorescent compound and said luminescence is fluorescence.

8. The method according to claim 7 wherein the turbid medium has a surface and the beam of light is substantially normal to the surface and is incident at a preselected position on the surface, and wherein the distance D1 is a radius of a first circle with said preselected position at the center of the first circle, and wherein the distance D2 is a radius of a second circle with said preselected position at the center of the second circle.

9. The method according to claim 8 wherein the fluorescent signal F is measured by a fluorescence detector means located on a circumference of the first circle of radius D1 and oriented so that it detects radiation emitted from the turbid medium substantially normal to the surface of the turbid medium, and wherein the reflectance signal R is measured by a reflectance detector means located on a circumference of the second circle of radius D2 and oriented so that it detects radiation emitted from the turbid medium substantially normal to the surface of the turbid medium.

10. The method according to claim 9 wherein the beam of light is produced from a light source having a first optical fiber connected thereto with the first optical fiber having a distal end portion placed on the surface of the turbid medium at the first preselected position, and wherein the fluorescence detector means has a second optical fiber attached thereto, the second optical fiber having a distal end portion placed on the circumference of the first circle of radius D1 on the surface, and wherein the reflectance detector means has a second optical fiber connected thereto, the third optical fiber having a distal end portion placed on the second circle of circumference D2 on the surface.

11. The method according to claim 10 wherein the distal end portions of the first, second and third optical fibers are connected to a holder having an adjustment mechanism for adjusting the distance D1 between the distal end portion of the first and second optical fibers and for adjusting the distance D2 between the distal end portion of the first and third optical fibers.

12. The method according to claim 11 wherein said turbid medium is mammalian tissue, and wherein D1 is in a range from about 0.84 mm to 0.88 mm and D2 is in a range from about 1.40 mm to about 1.45 mm.

13. The method according to claim 10 wherein measuring the reflectance signal R includes filtering reflectance signal so that only light of wavelength $\lambda_1$ is transmitted by said third optical fiber to the reflectance detector.

14. The method according to claim 10 wherein measuring the fluorescence signal F includes filtering light so that light of a preselected wavelength $\lambda_2 \neq \lambda_1$ is transmitted by said second optical fiber to the fluorescence detector.

15. The method according to claim 7 wherein the beam of light is produced from a light source having a first optical fiber connected thereto with the first optical fiber having a distal end portion for coupling the beam of light out of the first fiber, and wherein the fluorescent signal F is measured by a fluorescence detector means having a second optical fiber attached thereto, the second optical fiber including a distal end portion for coupling the fluorescent signal into the second fiber, and wherein the reflectance signal R is measured by a reflectance detector means having a second optical fiber attached thereto, the second optical fiber having a distal end portion for coupling the reflectance signal into the second fiber.

16. The method according to claim 15 wherein the three optical fibers are incorporated into a probe including a holder for holding the distal end portions of the three optical fibers and wherein the distance between the distal end portions of the first and second optical fibers is D1 and is adjustable, and wherein the distance between the distal end portions of the first and third optical fibers is D2 and is adjustable, and wherein the probe is insertable into a turbid medium.

17. The method according to claim 16 wherein the probe is a catheter, and wherein the turbid medium is biological tissue.

18. The method according to claim 17 wherein the biological tissue is blood.

19. The method according to claim 1 wherein the luminescent compound is a phosphorescent compound and said luminescence is phosphorescence.

20. A method of determining pairs of distances D1 and D2 for measuring luminescence and reflectance respectively in order to reduce effects of scattering and absorption variations between turbid samples, the distances D1 and D2 being measured from a beam of light used to induce luminescence in one or more luminescent compounds in the turbid medium, the method comprising the steps of;
   a) providing an effective reference turbid media having optical properties mimicking the turbid media and adding known amounts of a luminescent compound so as to increase the concentration of the luminescent compound and after addition of each known amount exciting the reference turbid medium with a beam of light at an effective wavelength and measuring a luminescence signal at a plurality of distances D1 from the beam of light and measuring a reflectance signal at a plurality of distances D2 from the beam of light;
   b) repeat step a) for an effective number of reference turbid media possessing a range of optical properties;
   c) for each pair of distances,
      plotting an effective function of both luminescence and reflectance (f(F, R)) versus concentration of the luminescent compound for all the reference turbid media and performing a regression analysis to calculate a best fit function and calculate a sum of squares of residuals; and
   d) identifying pairs of distances D1 and D2 corresponding to values of sum of squares of residuals lower than a threshold value for use in measuring luminescence and reflectance in the turbid medium in which concentration of the luminescent compound is to be determined.

21. The method according to claim 20 wherein the luminescent compound is a fluorescent compound and the luminescence is fluorescence.

22. The method according to claim 21 wherein effective function of the reflectance and fluorescence signals f(F, R)=F/R.

23. A method of measuring concentration of a fluorescent compound in a turbid medium including mammalian tissue, comprising:
   illuminating a mammalian tissue with a beam of light substantially perpendicular to a surface of the mammalian tissue, the excitation beam of light having an effective wavelength $\lambda_1$ to excite fluorescence in a fluorescent compound being detected in the mammalian tissue;
   measuring a fluorescence signal F at a wavelength $\lambda_2$ at a distance D1 from the beam of light, wherein D1 is in a range from about 0.84 mm to about 0.88 mm;
   measuring a reflectance signal R at wavelength $\lambda_1$ at a distance D2 from the beam of light, wherein D2 is in a range from about 1.40 mm to about 1.45 mm; and
   processing the measured R and F signals to produce an effective function f(F, R) and comparing f(F, R) to a calibration curve of $f_c(F_c, R_c)$ versus concentration of the fluorescent compound in a turbid medium to determine a concentration of the fluorescent compound.

24. The method according to claim 23 wherein the function f(F, R)=F/R and the calibration curve of $f_c(F_c, R_c)$ versus concentration of the fluorescent compound is determined by measuring a calibration fluorescence signal $F_c$ at D1 and a calibration reflectance signal $R_c$ at D2 in the turbid medium for a plurality of known concentrations of the fluorescent compound and plotting $F_c/R_c$ versus concentration of the fluorescent compound.

25. The method according to claim 24 wherein the fluorescence signal F is measured by a first detector means placed on the surface a distance D1 from the excitation beam of light and the reflectance signal R is measured by a second detector means placed on the surface a distance D2 from the beam of light.

26. The method according to claim 25 wherein the fluorescent signal F is measured with a first detector means having a first optical fiber attached thereto and the first optical fiber having a distal end portion placed in close proximity to the surface at the distance D1, and wherein the reflectance signal R is measured with a second detector means having a second optical fiber connected thereto and the second optical fiber having a distal end portion placed in close proximity to the surface at the distance D2.

27. The method according to claim 26 wherein the excitation beam of light originates from a light source having an optical fiber connected thereto with the optical fiber having a distal end portion placed in close proximity to a preselected position the surface and being substantially perpendicular thereto.

28. A method of theoretically calculating pairs of distances D1 and D2 for measuring luminescence and reflectance respectively in order to reduce effects of scattering and absorption variations between turbid samples, the distances D1 and D2 being measured from a beam of light used to induce luminescence in one or more fluorescent compounds in the turbid medium, the method comprising the steps of;
  a) for a series of increasing fluorophore concentrations, calculate fluorescence at a plurality of distances D1 from a hypothetical light source and calculate reflectance at a plurality of distances D2 from the hypothetical light source for a fixed concentration of fluorophore and for preselected values of the absorption and scattering coefficients of the turbid medium;
  b) repeat step a) for an effective number of turbid media possessing a range of absorption and scattering coefficients;
  c) for each pair of distances,
    plot an effective function of both fluorescence and reflectance (f(F, R)) versus concentration of the fluorescent compound for all the reference turbid media and perform a regression analysis to calculate a best fit function and calculate a sum of squares of residuals; and
  d) identify pairs of distances D1 and D2 corresponding to values of sum of squares of residuals lower than a threshold value for use in measuring fluorescence and reflectance in the turbid medium in which concentration of the fluorescent compound is to be determined.

29. The process according to claim 28 wherein the reflectance and fluorescence are calculated theoretically using a model such as Monte Carlo simulation, numerical solution of an effective radiation transport equation, or diffusion theory.

30. A device for measuring concentration of a fluorescent compound in tissue, comprising:
  a light source for producing a beam of light of wavelength $\lambda_1$;
  first detector means for measuring fluorescence;
  second detector means for measuring light of wavelength $\lambda_1$;
  a holder for holding the light source, first and second detector means, the holder including a planar portion adapted to be placed on a surface of a tissue and an adjustment mechanism for adjusting a distance between the light source and the first detector and a distance between the light source and the second detector; and
  processing means connected to said first and second detector means for processing measured fluorescence signals from said first and second detector means and calculating therefrom a concentration of a fluorescent compound in a tissue.

31. The device according to claim 30 wherein the light source has a first optical fiber attached thereto, the first optical fiber having a distal end portion for coupling the beam of light out of the first optical fiber, wherein the first detector means includes a second optical fiber attached thereto, the second optical fiber having a distal end portion for coupling a fluorescence signal into the optical fiber, wherein the second detector means includes a second optical fiber attached thereto, the second optical fiber having a distal end portion for coupling a reflectance signal into the optical fiber, and wherein the distal end portions of the first, second and third optical fibers are attached to the holder.

32. The device according to claim 31 wherein the adjustment mechanism adjusts the distance between the distal ends of the first and second optical fibers in a range from about 0.84 mm to about 0.88 mm.

33. The device according to claim 32 wherein the adjustment mechanism adjusts the distance between the distal ends of the first and third optical fibers in a range from about 1.40 mm to about 1.45 mm.

34. The device according to claim 31 wherein the second detector means includes filter means for filtering out all wavelengths except $\lambda_1$.

35. The device according to claim 31 wherein the first detector means includes filter means for filtering out all wavelengths except fluorescence signals at preselected wavelengths.

* * * * *